(12) United States Patent
Verdooner et al.

(10) Patent No.: US 9,566,000 B2
(45) Date of Patent: Feb. 14, 2017

(54) METHOD FOR DETECTING AMYLOID BETA PLAQUES AND DRUSEN

(71) Applicant: NeuroVision Imaging LLC, Sacramento, CA (US)

(72) Inventors: Steven Verdooner, Sacramento, CA (US); David Biggs, Sacramento, CA (US); Austin Blanco, Sacramento, CA (US)

(73) Assignee: NeuroVision Imaging LLC, Sacramento, CA (US)

( * ) Notice: Subject to any disclaimer, the term of this patent is extended or adjusted under 35 U.S.C. 154(b) by 0 days.

(21) Appl. No.: 14/208,881

(22) Filed: Mar. 13, 2014

(65) Prior Publication Data
US 2014/0268052 A1    Sep. 18, 2014

Related U.S. Application Data

(60) Provisional application No. 61/800,882, filed on Mar. 15, 2013.

(51) Int. Cl.
*A61B 3/14* (2006.01)
*A61B 3/10* (2006.01)

(52) U.S. Cl.
CPC .................... *A61B 3/102* (2013.01)

(58) Field of Classification Search
USPC ................................. 351/200–246
See application file for complete search history.

(56) References Cited

U.S. PATENT DOCUMENTS

| | | | |
|---|---|---|---|
| 2009/0244485 A1* | 10/2009 | Walsh | A61B 3/102 351/221 |
| 2011/0208064 A1* | 8/2011 | Chongzhao | A61K 49/0021 600/476 |
| 2012/0229766 A1 | 9/2012 | Russmann | |
| 2012/0251452 A1 | 10/2012 | Verdooner | |
| 2013/0130288 A1* | 5/2013 | Goure et al. | 435/7.94 |
| 2015/0116662 A1* | 4/2015 | Wada | A61B 3/0025 351/206 |

OTHER PUBLICATIONS

Robinson M. Dirk, New Applications of Super-resolution in Medical Imaging, CRC Press, 2010, p. 15-21 (http://people.duke.edu/~sf59/MedicaL_SR_chapter10.pdf).

Jennifer H. Acton, Drusen detection in retro-mode imaging by a scanning laser ophthalmoscope, Acta Ophthalmologica, 2011, 89, p. e404-e411 (http://onlinelibrary.wiley.com/doi/10.1111/j.1755-3768.2011.02123.x/pdf).

* cited by examiner

*Primary Examiner* — Mohammed Hasan
(74) *Attorney, Agent, or Firm* — Lucas & Mercanti, LLP; Peter J. Phillips

(57) ABSTRACT

A method for detecting amyloid beta plaques and drusen is disclosed. The method for detecting amyloid beta plaques and drusen may include applying a combination of optical retro mode illumination techniques to acquire a plurality of amyloid beta plaques and drusen images that are too small to be seen with other imaging modalities. The amyloid beta plaques and drusen images may also be detected with a non-transitory computer storage media having instructions stored thereon which, when executed, execute the method for detecting amyloid beta plaques and drusen. The method may track changes in plaque, size, area and density of the amyloid beta plaques and drusen over a predetermined period of time.

20 Claims, 5 Drawing Sheets

400

Utilizing an annual aperture with a central stop that deviates laterally from a confocal light path
410

Blocking directly reflected light from a fundus with only laterally scattered light passing through the annular aperture, thereby imaging the one or more amyloid beta plaques and drusen
420

Identifying the imaged one or more amyloid beta plaques and drusen in a retinal structure and a pathology
430

Applying a combination of optical retro mode illumination techniques to the imaged one or more amyloid beta plaques and drusen
440

Detecting the imaged one or more amyloid beta plaques and drusen that are too small to be seen with other imaging modalities
450

FIG. 4

METHOD FOR DETECTING AMYLOID BETA PLAQUES AND DRUSEN

This application claims priority to U.S. Provisional Application 61/800,882 filed on Mar. 15, 2013, the entire disclosure of which is incorporated by reference.

BACKGROUND OF THE INVENTION

Field of the Invention

The present invention is a method for detecting. More specifically, the present invention is a method for detecting amyloid beta plaques and drusen.

Description of the Related Art

Drusen are early fundus changes characteristic of age-related maculopathy. Early detection of maculopathy and also Alzheimer's disease with amyloid beta or AB plaques is vitally important to early intervention and treatment. Conventional fundus photography is widely utilized in imaging and detecting drusen. There currently is no method for AB plaque detection except with the utilization of specialized dye and other contrast agents.

Optical coherence tomography or OCT is also an imaging technique that is utilized whereby retinal structures may be viewed in cross-section. Relatively larger drusen are visible in OCT images as elevations of retinal pigment epithelium or RPE. The utilization of infrared imaging is much more comfortable and advantageous in elderly patients with lens opacities, since light is scattered relatively much less in the presence of media opacities. Retro-mode imaging in a confocal scanning laser ophthalmoscope or SLO is utilized to image the retina with an infrared laser. It is based on indirect mode imaging of a SLO.

BRIEF SUMMARY OF THE INVENTION

The present invention is a method for detecting. More specifically, the present invention is a method for detecting amyloid beta plaques and drusen.

The method for detecting amyloid beta plaques and drusen may include means for imaging a plurality of frames of multiple views of a central portion and a peripheral portion of the patient user's retina, means for aligning and combining the frames utilizing one or more super-resolution techniques, means for monitoring the aligned and combined frames and means for quantifying changes in the monitored, aligned and combined frames.

The method for detecting amyloid beta plaques and drusen may include the steps of utilizing an annual aperture with a central stop that deviates laterally from a confocal light path, blocking directly reflected light from a fundus with only laterally scattered light passing through the annular aperture, thereby imaging the one or more amyloid beta plaques and drusen, identifying the imaged one or more amyloid beta plaques and drusen in a retinal structure and a pathology, applying a combination of optical retro mode illumination techniques to the imaged one or more amyloid beta plaques and drusen and detecting the imaged one or more amyloid beta plaques and drusen that are too small to be seen with other imaging modalities.

A non-transitory computer storage media having instructions stored thereon which, when executed, execute a method for detecting amyloid beta plaques and drusen may include the steps of utilizing an annual aperture with a central stop that deviates laterally from a confocal light path, blocking directly reflected light from a fundus with only laterally scattered light passing through the annular aperture, thereby imaging the one or more amyloid beta plaques and drusen, identifying the imaged one or more amyloid beta plaques and drusen in a retinal structure and a pathology, applying a combination of optical retro mode illumination techniques to the imaged one or more amyloid beta plaques and drusen and detecting the imaged one or more amyloid beta plaques and drusen that are too small to be seen with other imaging modalities.

It is an object of the present invention to provide a method for detecting amyloid beta plaques and drusen that may detect relatively smaller amyloid beta plaques than conventional detection methods.

It is an object of the present invention to provide a method for detecting amyloid beta plaques and drusen that may utilize a combination of optical retro mode illumination techniques utilizing a confocal laser scanning ophthalmoscope and one or more super-resolution image processing techniques to detect one or more plaques at an early stage of pathology.

It is an object of the present invention to provide a method for detecting amyloid beta plaques and drusen that detect pathologies such as dry macular degeneration and Alzheimer's disease.

It is an object of the present invention to provide a method for detecting amyloid beta plaques and drusen that tracks changes in a pathology that includes changes in plaque, size, area and density over time.

BRIEF DESCRIPTION OF THE DRAWINGS

The present invention will be described by way of exemplary embodiments, but not limitations, illustrated in the accompanying drawing in which like references denote similar elements, and in which:

FIG. 4 illustrates a flowchart of a second method for detecting amyloid beta plaques and drusen, in accordance with one embodiment of the present invention.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

While the present invention has been related in terms of the foregoing embodiments, those skilled in the art will recognize that the invention is not limited to the embodiments described. The present invention may be practiced with modification and alteration within the spirit and scope of the appended claims. Thus, the description is to be regarded as illustrative instead of restrictive on the present invention.

Figure 1:
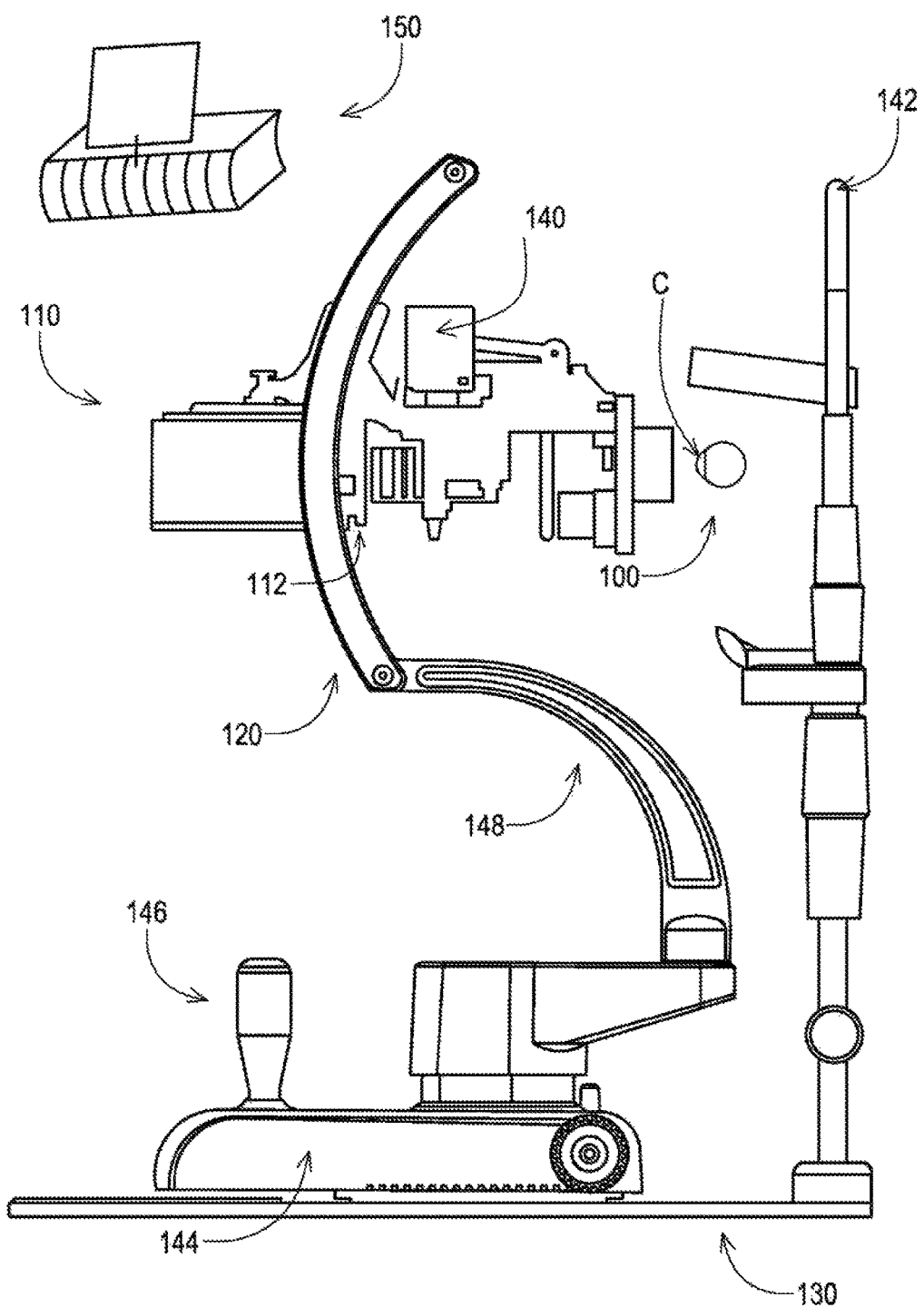
FIG. 1 illustrates a side perspective view of an apparatus for imaging an eye utilized in combination with a computer, in accordance with one embodiment of the present invention.

FIG. 1 illustrates an exploded perspective view of an apparatus for producing an image of an eye 100, in accordance with one embodiment of the present invention.

The apparatus for producing an image of an eye 100 includes a video camera 110, video camera optics 112, a camera housing 120 mounted on a slit lamp chinrest and joystick assembly 130 and illumination source optics 140. The video camera 110 is a digital camera but can be any type of suitable camera for use with the apparatus for producing an image of an eye 100. The slit lamp chinrest and joystick assembly 130 includes a head support 142, a movable base 144, a joystick 146, and a housing support 148. The head support 142 holds the patient's chin and forehead in a known, fixed position. The head support 142 is provided with elevation adjustments to provide a comfortable resting place for the patient's head. The position of the camera housing 120 relative to the head support 142 can be adjusted in both relative gross and fine increments using the joystick 146. The apparatus for producing an image of an eye 100 is used in combination with a computer system 150, which is described in greater detail in FIG. 1D. The computer system 150 can be any suitable computer system 150 that can be used in combination with the apparatus for imaging an eye 100.

The personal computer 150 forms the center of the apparatus for imaging an eye 100, processing data and controlling the operation of other components of the apparatus for imaging an eye 100. Connected to the personal computer 150 is a video camera 110. An observation video monitor which can be the screen of the personal computer, a slit lamp chinrest and joystick assembly 130, illumination source optics 140, and video camera optics 112 are associated with the camera housing 120. The personal computer 150 is preferably a relatively compact computer, embedded computer, or tablet computer of relatively high processing power using a standardized operating system and having standardized card slots for interfacing peripheral equipment such as memory cards, video board, printer and a monitor. The personal computer 150 will run customized software as will be described in detail later. The monitor or screen of the personal computer will have very-high-resolution color graphics capability appropriate for displaying images under analysis.

The digitizing board accepts a digital file or video input from video camera 110 and functions as a "frame grabber," or display. That is, when activated by a signal from the personal computer 150, the digitizing board will collect video and/or digital data and images from video camera 110 at that instant and store into digital data. The digital data produced is stored in memory and made available to personal computer 150 for analysis.

Figure 2:
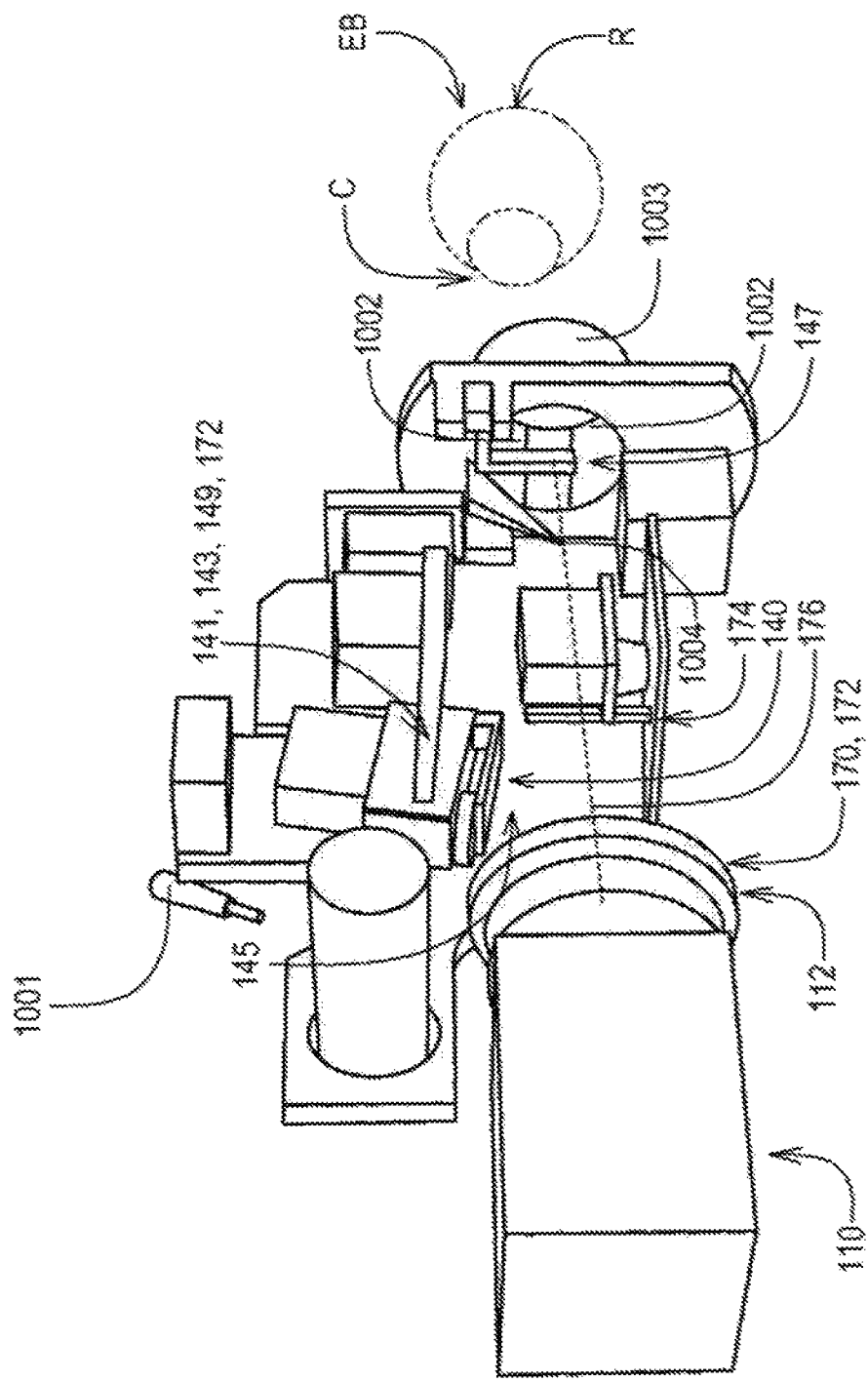
FIG. 2 illustrates a side perspective view of a camera housing, in accordance with one embodiment of the present invention.

FIG. 2 illustrates a side perspective view of a camera housing 120 of the chinrest and joystick assembly 130, in accordance with one embodiment of the present invention. The camera housing 120 containing the video camera 110 illumination source(s) and optics 140 is proximate to a sectioned patient eyeball EB with a cornea C and a retina R. Housing 120 may be cylindrical or of any other suitable shape. The housing 120 has no forward protruding parts, which prevents accidental direct contact of any part of the apparatus for imaging an eye 100 with the patient's cornea C or facial features during movement of the housing 120 relative to the patient's eyes. This is advantageous since there is no contact with the patient's cornea C to accomplish examination and image capture. The external housing 120 and the optics have been designed to maintain some distance to the cornea C, increasing patient comfort while any testing is being performed. A flexible interface such as a rubber cup 180 can be provided at the interface between the housing 120 and the patient's eyeball EB. The inclusion of illumination source optics 140, camera optics 112 and the video camera 110 in the camera housing 120 provides a high degree of accessibility. By placing all elements of the apparatus for imaging an eye 100 in one camera housing 120, allows for an affordable design. Additionally, the relatively small design of the apparatus for imaging an eye 100 compared to that of a fundus camera for observation and image capture provides for a shorter and more efficient optical pathway. The compact design and simplicity of optics 112,140 reduces production costs and permits greater ease of use by the operator. The design of the apparatus for imaging an eye 100 allows imaging through a smaller pupil as compared to a fundus camera. Video camera 110 is relatively compact and incorporates a color or monochrome CCO, CMOS, or multi hyper-spectral image sensor. The focus of the patient may also be achieved by focus of internal optical elements of the digital camera. Lens contained inside camera 100 may be focused automatically or manually by observing the image displayed on an observation video monitor. Alternatively, an electronic auto-focusing control system could be provided for automatically adjusting the focus of lens inside camera 100. The video camera 110 can also contain a monochrome or color CCO or CMOS sensor (not shown).

The observation optics 112 associated with the video camera 110 include the lens 170, an observation aperture 172, and a filter 174. The observation aperture 172 and the filter 174 transmit light reflected from the retina R to the lens 170 and to the video camera 110. The filter 174 is an infrared stepping filter (or other filter for other imaging procedures) which improves the contrast of the image seen by the video camera 110. Indo-cyanine green angiography, color fundus photography, auto-fluorescence, or fluorescein angiography, curcumin fluorescence imaging, or other filter sets may be utilized by the apparatus for imaging an eye 100. These filters will be mounted so as to be selectively rotatable in and out of the view axis of the video camera 110 according to the function being performed. The rotation may be accomplished manually or under computer servo control. The projection optics 140 of the invention projects light onto the retina R, off axis at an angle to the central axis 176 of lens 170 of video camera 110. The projection optics 140 includes a lamp 141, a lamp lens group 143, a mirror 145, and a projection aperture 172. A control 1001 is provided to adjust the intensity and position of the lamp 141, either manually or under the control of the computer system 150. The control is also used to sequentially control multiple lamps 141, shifting optical elements, and flipping masks 147, LED flipping internal fixation pointer 1004, and image capture trigger.

The light from lamp 141 passes through aperture 149 and the series of lamp lens group 143 that typically has two lenses. The lenses of lamp lens group 143 concentrate the light output of lamp 141. Lamp lens group 143 may preferably consist of multiple lenses or a single aspheric lens. The light is then deflected by mirror 145 which is placed at a critical pitch angle relative to the video camera 110 and the projection optics 112. The light passes from the mirror 145 past the flipping mask 147 which concentrates the light. The light then passes through a plurality of small pupil masks 1002. The light then passes through the objective lens 1003. The light then passes past the cornea C and is projected onto retina R. All the masks and apertures used, such as flipping mask 147 and aperture 149 and 1002, are appropriately sized apertures. Although the lamp 141 has been described as a generalized LED lamp, it should be noted that the lamp 141 can be any source of radiant energy. In one preferred embodiment, the lamp 141 is an infrared illumination source, and the specifications of filter 174 are adjusted accordingly to pass the wavelength of the lamp 141. Infrared illumination may be particularly desirable for alignment prior to acquiring images without the problems generated by lack of pupil dilation. The image can be captured in a relatively dark room using infrared illumination, so that the eye being imaged is naturally dilated. In another preferred embodiment which addresses the problems caused by lack of pupil dilation during imaging, the lamp 141 may be strobed in full color, red free, NIR or other preferred wavelength (based on imaging procedure desired) during image acquisition rather than being kept on constantly, thereby preventing the energy of lamp 141 from narrowing the pupil prior to image capture. Because of the unique design of the projection optics 140 and the capabilities of the image processing and analysis software employed, useful image data from each image can be collected with minimum pupil dilation. Specifically, the pupils of the eye being imaged may have a diameter of as little as 2 mms. The projection optics 140 projects light onto the retina R off axis from the observation path of video camera 110. Another preferred embodiment places an adjustable mask 1002 adjacent to objective lens 1003 that adjust to the patient's pupil to optimize the image when the pupil is small.

Figure 3:
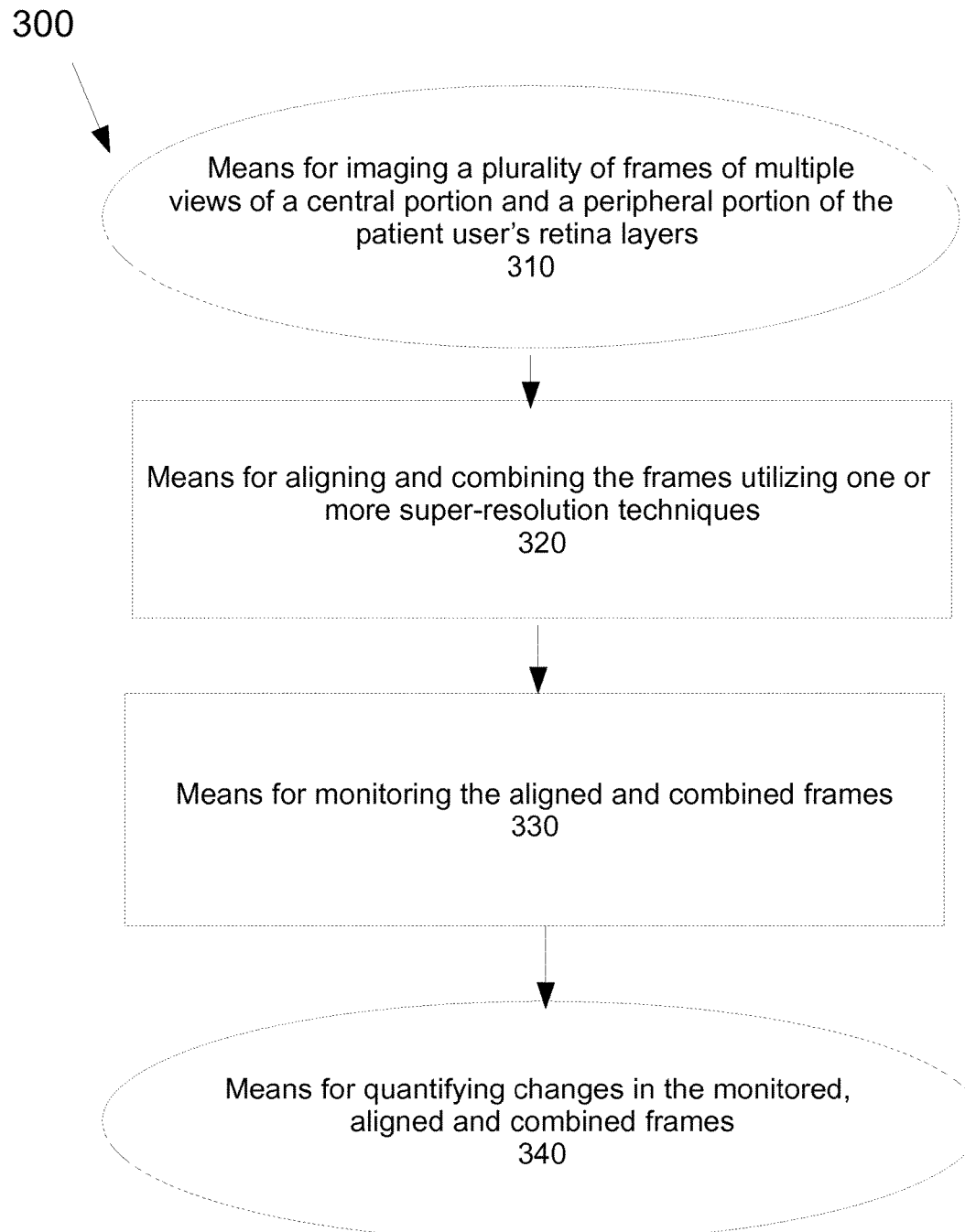
FIG. 3 illustrates a flowchart of a first method for detecting amyloid beta plaques and drusen, in accordance with one embodiment of the present invention.

FIG. 3 illustrates a flowchart of a first method 300 for detecting amyloid beta plaques and drusen, in accordance with one embodiment of the present invention.

The overall first method 300 may include means for imaging a plurality of frames of multiple views of a central portion and a peripheral portion of the patient user's retina 310, means for aligning and combining the frames utilizing one or more super-resolution techniques 320, means for monitoring the aligned and combined frames 330 and means for quantifying changes in the monitored, aligned and combined frames 340.

The means for imaging 310 may utilize an optical coherence tomography or OCT imaging technique that is utilized whereby retinal structures may be viewed in cross-section. The means for aligning and combining 320 may utilize a combination of optical retro mode illumination techniques utilizing a confocal laser scanning ophthalmoscope and one or more super-resolution image processing techniques. The means for monitoring the aligned and combined frames 330 may be performed by a non-transitory storage media that receives the retinal structures viewed in cross-section from the optical coherence tomography imaging technique and confocal laser scanning ophthalmoscope and one or more super-resolution image processing techniques. The non-transitory storage media may be executed by a processor and a memory system. The means for quantifying 340 may also be performed by the non-transitory storage media.

FIG. 4 illustrates a flowchart of a second method 400 for detecting amyloid beta plaques and drusen, in accordance with one embodiment of the present invention.

The second method 400 may include the steps of utilizing an annual aperture with a central stop that deviates laterally from a confocal light path 410, blocking directly reflected light from a fundus with only laterally scattered light passing through the annular aperture, thereby imaging the one or more amyloid beta plaques and drusen 420, identifying the imaged one or more amyloid beta plaques and drusen in a retinal structure and a pathology 430, applying a combination of optical retro mode illumination techniques to the imaged one or more amyloid beta plaques and drusen 440 and detecting the imaged one or more amyloid beta plaques and drusen that are too small to be seen with other imaging modalities 450.

The utilizing step 410 may include utilizing an optical coherence tomography or OCT imaging technique that is utilized whereby retinal structures may be viewed in cross-section. The blocking step 420 may include utilizing an optical coherence tomography or OCT imaging technique that is utilized whereby retinal structures may be viewed in cross-section. The identifying step 430 may include the pathology that is Alzheimer's disease or the pathology that is dry macular degeneration. The applying step 440 may include the optical retro mode illumination techniques that may include a confocal laser scanning ophthalmoscope and one or more super-resolution image processing techniques. The one or more super-resolution image processing techniques may be multi-image super-resolution image processing techniques. The detecting step 450 may include tracking changes in the pathology over a predetermined period time. The tracking changes may include plaque, size, area and density over the predetermined period of time.

Figure 5:
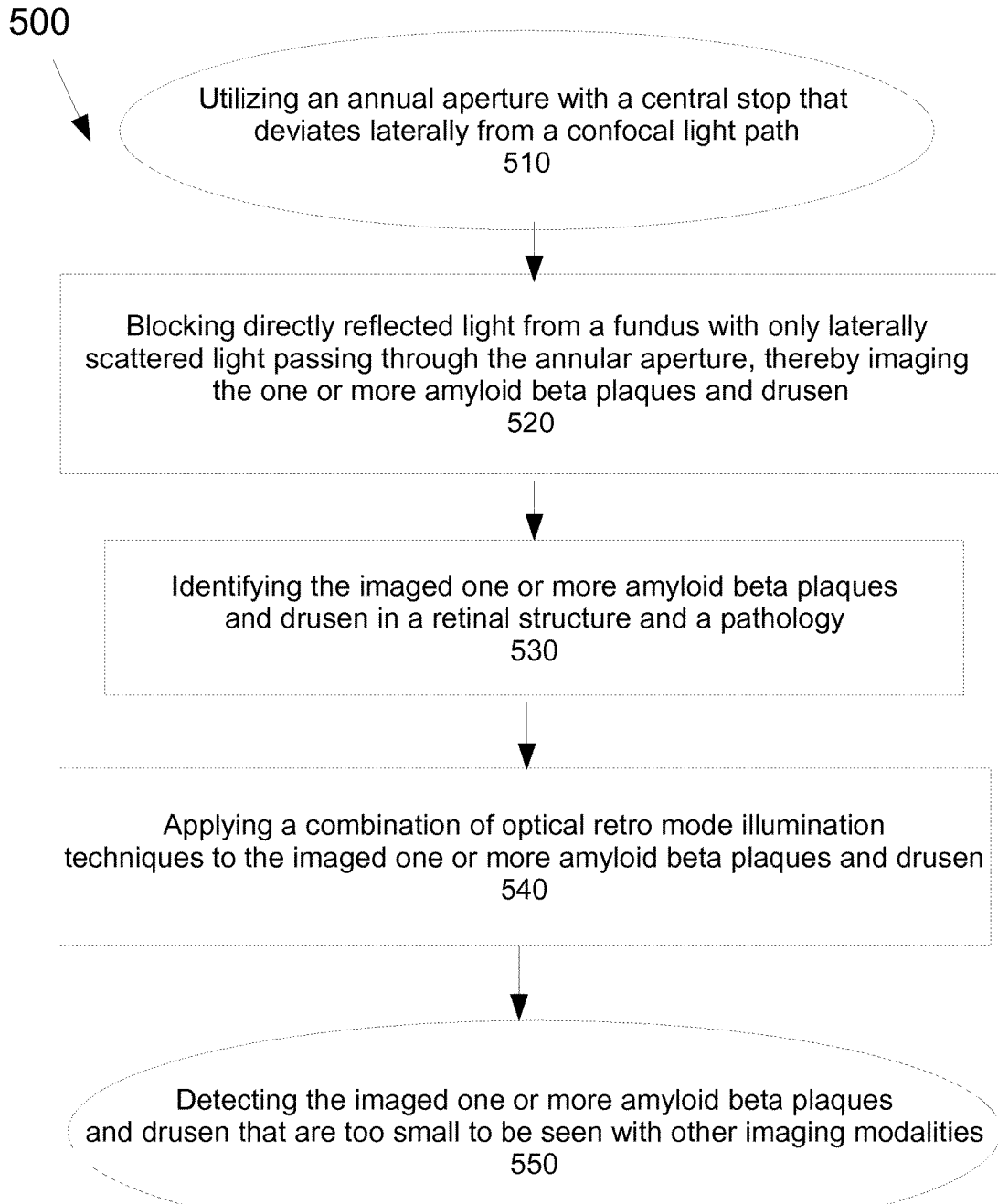
FIG. 5 illustrates a flowchart of a method for detecting amyloid beta plaques and drusen by a non-transitory computer storage media having instructions stored thereon which, when executed, execute the method, in accordance with one embodiment of the present invention.

FIG. 5 illustrates a flowchart of a method 500 for detecting amyloid beta plaques and drusen by a non-transitory computer storage media having instructions stored thereon which, when executed, execute the method 500, in accordance with one embodiment of the present invention.

The non-transitory computer storage media may include the steps of utilizing an annual aperture with a central stop that deviates laterally from a confocal light path 510, blocking directly reflected light from a fundus with only laterally scattered light passing through the annular aperture, thereby imaging the one or more amyloid beta plaques and drusen 520, identifying the imaged one or more amyloid beta plaques and drusen in a retinal structure and a pathology 530, applying a combination of optical retro mode illumination techniques to the imaged one or more amyloid beta plaques and drusen 540 and detecting the imaged one or more amyloid beta plaques and drusen that are too small to be seen with other imaging modalities 550.

The utilizing step 510 may include utilizing an optical coherence tomography or OCT imaging technique that is utilized whereby retinal structures may be viewed in cross-section. The blocking step 520 may include utilizing an optical coherence tomography or OCT imaging technique that is utilized whereby retinal structures may be viewed in cross-section. The identifying step 530 may include the pathology that is Alzheimer's disease or the pathology that is dry macular degeneration. The applying step 540 may include the optical retro mode illumination techniques that may include a confocal laser scanning ophthalmoscope and one or more super-resolution image processing techniques. The one or more super-resolution image processing techniques may be multi-image super-resolution image processing techniques. The detecting step 550 may include tracking changes in the pathology over a predetermined period time. The tracking changes may include plaque, size, area and density over the predetermined period of time.

The method for detecting amyloid beta plaques and drusen may utilize an annular aperture with a central stop that deviates laterally from a confocal light path. Directly reflected light emitted towards a fundus may be blocked by a central stop with only scattered light passing through the annular aperture. Laterally scattered light may be sampled more than light in a direct mode. Retinal structures and pathology may be detected with the only laterally scattered light. Drusen and AB plaques may be imaged with this technique due to increase in scatter. While the method may be helpful in detection of large plaques, the combination of the method with super-resolution and other image processing and analysis techniques may yield a method that may detect relatively much smaller plaques at relatively earlier stages of pathology and may also be tracked over time. Amyloid beta plaque and drusen may be identified in a retinal structure however identification of the deposits at relatively earlier stages of disease and of a relatively small size is impossible with existing retinal imaging technology. This problem may be solved through a combination of optical retro mode illumination techniques utilizing a confocal laser scanning ophthalmoscope in combination with super-resolution image processing techniques that detect relatively very small plaques that are too small to be seen with other imaging modalities. Utilizing retro mode imaging alone does yield some imaging of drusen, AB plaques and other deposits that are relatively small in size but do not reliably image relatively small to very small plaques. Multi-image super-resolution techniques may record a series of images and then combine a data set from the series of images to produce images of relatively greatly improved resolution and image quality thereby resolving the relatively smallest plaques at the relatively earliest stages of disease. Furthermore, tracking changes in plaque, size, area and density over a predetermined period of time is likely an indicator of advancing disease and rate of advancing disease. These aspects have never been previously studied.

Multiple images may be acquired utilizing each of the retro-mode illumination techniques. These images may be transferred to a software or non-transitory storage media to co-registers each of the images. The non-transitory storage media may process the images to increase contrast where intensity shifts occur. The non-transitory storage media may increase a signal by subtracting noise. The subtracted noise may be accomplished by referencing numerous modal images and producing a result where the noise or artifact error from each type of retro mode is removed leaving only the combined signal structures from each retro mode image. The resulting super resolution image may be relatively highly improved over each individual retro mode image and by reducing the signal and building the noise in the individual retro mode image, higher detection sensitivity may be achieved in the final image. A high bit depth final image of approximately eight bits or more may be produced which may be analyzed utilizing conventional methods.

In another embodiment fluorescent emission images may be combined with retro-mode images to produce a co-located detection matrix.

In another embodiment, standard confocal infrared or IR images may be combined with retro-mode images to produce a higher sensitivity traditional confocal image or to produce a hyper-contrast combination image.

In another embodiment, an annual aperture utilized in the retromode may be replaced with a slit, grid, holographic interference image or coded aperture to further increase detection of traditionally sub-resolvable spots.

In another embodiment, multiple focal planes may be acquired and combined, to produce a three-dimensional render of the detected spots.

In another embodiment the aperture position may be stepped in the optical path, to alter its interaction with the reflected or emitted light from a subject.

In another embodiment the method may be utilized for a variety of imaging procedures including color fundus imaging, fluorescein angiography, I ndocyanine Green or ICG angiography, red-free, infrared or IR retro-illumination, hyper spectral and multi-spectral imaging, and devices that are utilized in combination with OCT.

The method for detecting amyloid beta plaques and drusen will be utilized for the detection and advancement of dry macular degeneration and Alzheimer's disease. The method includes imaging a plurality of frames of multiple views of a central portion and a peripheral portion of a patient user's retina, aligning and combining the frames utilizing one or more super-resolution techniques, monitoring the aligned and combined frames and quantifying changes in the monitored, aligned and combined frames. The changes in the aligned and combined frames may be tracked over a predetermined period of time such as a day, a week, a month, a year or other suitable predetermined period of time.

What is claimed is:

1. A method for detecting one or more amyloid beta plaques and drusen in a patient user's retina, comprising:
    means for imaging a plurality of frames of multiple views of a central portion and a peripheral portion of the patient user's retina;
    means for aligning and combining the frames utilizing one or more super-resolution techniques;
    means for monitoring the aligned and combined frames; and
    means for quantifying changes in the monitored, aligned and combined frames.

2. The method according to claim 1, wherein the means for imaging utilizes an optical coherence tomography imaging technique.

3. The method according to claim 1, wherein the means for aligning and combining utilizes a combination of one or more optical retro mode illumination techniques and one or more super-resolution image processing techniques.

4. The method according to claim 3, wherein the combination of one or more optical retro mode illumination techniques and one or more super-resolution image processing techniques utilizes a confocal laser scanning ophthalmoscope.

5. The method according to claim 1, wherein the means for monitoring and the means for quantifying is performed by a non-transitory storage media, a processor and a memory system.

6. The method according to claim 1, wherein the method detects Alzheimer's disease and dry macular degeneration.

7. A method for detecting one or more amyloid beta plaques and drusen, comprising the steps of:
utilizing an annular aperture with a central stop that deviates laterally from a confocal light path;
blocking directly reflected light from a fundus with only laterally scattered light passing through the annular aperture, thereby imaging the one or more amyloid beta plaques and drusen;
identifying the imaged one or more amyloid beta plaques and drusen in a retinal structure and pathology;
applying a combination of optical retro mode illumination techniques to the imaged one or more amyloid beta plaques and drusen;
and detecting the imaged one or more amyloid beta plaques and drusen that are too small to be seen with other imaging modalities.

8. The method according to claim 7, wherein the pathology is Alzheimer's disease.

9. The method according to claim 7, wherein the pathology is dry macular degeneration.

10. The method according to claim 7, wherein the optical retro mode illumination techniques includes a confocal laser scanning ophthalmoscope and one or more super-resolution image processing techniques.

11. The method according to claim 10, wherein the one or more super-resolution image processing techniques are multi-image super-resolution image processing techniques.

12. The method according to claim 7, wherein the method tracks changes in the pathology over a predetermined period time.

13. The method according to claim 12, wherein changes include tracking changes in plaque, size, area and density over the predetermined period of time.

14. A non-transitory computer storage media having instructions stored thereon which, when executed, execute a method comprising the steps of:
utilizing an annual aperture with a central stop that deviates laterally from a confocal light path;
blocking directly reflected light from a fundus with only laterally scattered light passing through the annular aperture, thereby imaging the one or more amyloid beta plaques and drusen;
identifying the imaged one or more amyloid beta plaques and drusen in a retinal structure and pathology;
applying a combination of optical retro mode illumination techniques to the imaged one or more amyloid beta plaques and drusen;
and detecting the imaged one or more amyloid beta plaques and drusen that are too small to be seen with other imaging modalities.

15. The non-transitory computer storage media according to claim 14, wherein the pathology is Alzheimer's disease.

16. The non-transitory computer storage media according to claim 14, wherein the pathology is dry macular degeneration.

17. The non-transitory computer storage media according to claim 14, wherein the optical retro mode illumination techniques include a confocal laser scanning ophthalmoscope and one or more super-resolution image processing techniques.

18. The non-transitory computer storage media according to claim 17, wherein the one or more super-resolution image processing techniques are multi-image super-resolution image processing techniques.

19. The non-transitory computer storage media according to claim 14, wherein the method tracks changes in the pathology over a predetermined period time.

20. The non-transitory computer storage media according to claim 19, wherein changes include tracking changes in plaque, size, area and density over the predetermined period of time.

* * * * *